(12) United States Patent
Hong et al.

(10) Patent No.: US 12,404,228 B2
(45) Date of Patent: Sep. 2, 2025

(54) METHOD OF PRODUCING ADIPIC ACID

(71) Applicants: HYUNDAI MOTOR COMPANY, Seoul (KR); KIA CORPORATION, Seoul (KR); KOREA RESEARCH INSTITUTE OF CHEMICAL TECHNOLOGY, Daejeon (KR)

(72) Inventors: Chae Hwan Hong, Seoul (KR); Hyeon Gook Kim, Daejeon (KR)

(73) Assignees: HYUNDAI MOTOR COMPANY, Seoul (KR); KIA CORPORATION, Seoul (KR); KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 462 days.

(21) Appl. No.: 18/111,018

(22) Filed: Feb. 17, 2023

(65) Prior Publication Data

US 2024/0092717 A1  Mar. 21, 2024

(30) Foreign Application Priority Data

Sep. 7, 2022 (KR) ........................ 10-2022-0113326

(51) Int. Cl.
*C07C 51/09* (2006.01)
*C07C 67/327* (2006.01)

(52) U.S. Cl.
CPC ............ *C07C 51/09* (2013.01); *C07C 67/327* (2013.01)

(58) Field of Classification Search
CPC ....... C07C 51/09; C07C 67/327; C07C 55/14; C07C 69/44
See application file for complete search history.

(56) References Cited

U.S. PATENT DOCUMENTS

| | | |
|---|---|---|
| 8,669,397 B2 | 3/2014 | Boussie et al. |
| 2016/0311746 A1 | 10/2016 | Pinkos et al. |
| 2017/0001944 A1 | 1/2017 | Zhang et al. |

FOREIGN PATENT DOCUMENTS

| | | |
|---|---|---|
| CN | 107556186 B | 6/2019 |
| CN | 111440060 A | 7/2020 |
| CN | 111233657 B | 8/2021 |
| WO | 2010/144862 A2 | 12/2010 |
| WO | 2017/147098 A1 | 8/2017 |

*Primary Examiner* — Deborah D Carr
(74) *Attorney, Agent, or Firm* — MCDONNELL BOEHNEN HULBERT & BERGHOFF LLP

(57) ABSTRACT

A method of producing adipic acid using glucose as a starting material, in which adipic acid is finally obtained via an alkyl adipate intermediate from a glucaric acid potassium salt.

16 Claims, 3 Drawing Sheets

METHOD OF PRODUCING ADIPIC ACID

CROSS REFERENCE TO RELATED APPLICATIONS

This application claims, under 35 U.S.C. § 119(a), the benefit of priority from Korean Patent Application No. 10-2022-0113326, filed on Sep. 7, 2022, the entire contents of which are incorporated herein by reference.

BACKGROUND

(a) Technical Field

The present disclosure relates to a method of producing adipic acid.

(b) Background Art

Research and development of biomass, which is regarded as a future resource, is increasingly being emphasized. Recently, various methods of preparing biomaterials and chemicals are being developed worldwide.

The materials for use in interiors and exteriors and engine chassis parts currently used in automobiles include polypropylene (PP), nylon, polycarbonate (PC), acrylonitrile butadiene styrene (ABS), and the like. Thereamong, polypropylene is used in the largest amount, followed by nylon. For example, among nylon materials, nylon 66 is being applied in an amount of about 15 kg per automobile.

Therefore, a significant spillover effect may be expected if this highly versatile nylon production technology is advanced based on biomass. In particular, the current method of synthesizing petroleum-based adipic acid is a synthesis method that emits large amounts of greenhouse gases, and as such, there is a problem in view of carbon emission reduction.

Nylon 66 is in high demand due to excellent properties thereof, but production thereof using biomass as a raw material has not yet been established. Thus, the development of a process for producing bio-nylon 66 may be expected to have a great spillover effect not only economically but also environmentally. Nylon 66 has excellent heat resistance, wear resistance, and chemical resistance, and is thus used for parts requiring high-temperature characteristics among automobile parts. Among nylons used in automobile parts, nylon 66 is the second most used after nylon 6.

Nylon 66 is formed by dehydration polymerization of hexamethylenediamine and adipic acid. Here, the adipic acid monomer is currently produced through a chemical synthesis process using cyclohexanone that is obtained as an intermediate from benzene during crude oil refinement, starting from crude oil. As such, large amounts of greenhouse gases are emitted. Therefore, there is a need for a synthesis method using plant resources rather than a chemical process.

SUMMARY

The present disclosure has been made keeping in mind the problems encountered in the related art, and an object of the present disclosure is to provide a method of synthesizing adipic acid from glucose as a carbon-emission-reducing plant source, which realizes a carbon emission reduction effect and exhibits improved synthesis processing efficiency.

The objects of the present disclosure are not limited to the foregoing. The objects of the present disclosure will be able to be clearly understood through the following description and to be realized by the means described in the claims and combinations thereof.

In order to accomplish the above object, the present disclosure provides a method of producing adipic acid including obtaining a reaction solution by mixing a glucaric acid potassium salt, a solvent, an acid catalyst, and a catalyst for deoxydehydration, obtaining alkyl adipate by adding hydrogen gas to the reaction solution and performing a deoxydehydration (DODH) reaction, and obtaining adipic acid by mixing the alkyl adipate with an acid solution and performing a hydrolysis reaction.

The glucaric acid potassium salt may be obtained by mixing and reacting glucose, nitric acid, sodium nitrite, and potassium hydroxide.

The solvent may include methanol or ethanol.

The acid catalyst may include at least one selected from the group consisting of Amberlyst 15, 2,4-dinitrosulfonic acid, sulfuric acid, benzenesulfonic acid, trifluoromethanesulfonic acid, p-toluenesulfonic acid, and combinations thereof.

The weight ratio of the glucaric acid potassium salt to the acid catalyst may be about 5:7.5-8.5.

The catalyst for deoxydehydration may include at least one selected from the group consisting of rhenium oxide and LxReOy (in which L is amine, halogen, phenylsilyl, phosphine, alkoxy having 1 to 10 carbon atoms, alkyl having 1 to 10 carbon atoms, or COOR (in which R is an alkyl having 1 to 10 carbon atoms), and x and y are each independently an integer of 1 to 3, x+y=4).

The weight ratio of the glucaric acid potassium salt to the catalyst for deoxydehydration may be about 5:3.5-4.5.

The hydrogen gas may be added at a pressure of about 1 bar to 20 bar.

The alkyl adipate may be represented by Chemical Formula 1 below.

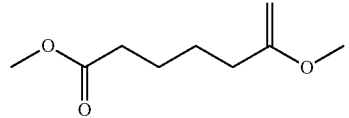

Chemical Formula 1

The alkyl adipate may be represented by Chemical Formula 2 below.

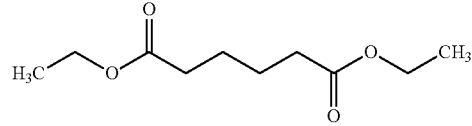

Chemical Formula 2

The alkyl adipate may be represented by Chemical Formula 3 below.

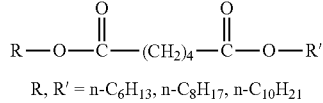

Chemical Formula 3

R, R' = n-$C_6H_{13}$, n-$C_8H_{17}$, n-$C_{10}H_{21}$

In the method, obtaining the alkyl adipate may be performed at a temperature of about 80° C. to 150° C.

In the method, obtaining the alkyl adipate may be performed for a period of time of about 12 hours to 24 hours.

The acid solution may include hydrochloric acid.

The concentration of the acid solution may be about 1 N to 5 N.

The weight ratio of the alkyl adipate to the acid solution may be about 1:5.5-6.5.

BRIEF DESCRIPTION OF THE FIGURES

The above and other features of the present disclosure will now be described in detail with reference to certain exemplary embodiments thereof illustrated in the accompanying drawings, which are given hereinbelow by way of illustration only, and thus are not limitative of the present disclosure, and wherein.

DETAILED DESCRIPTION

Figure 1:
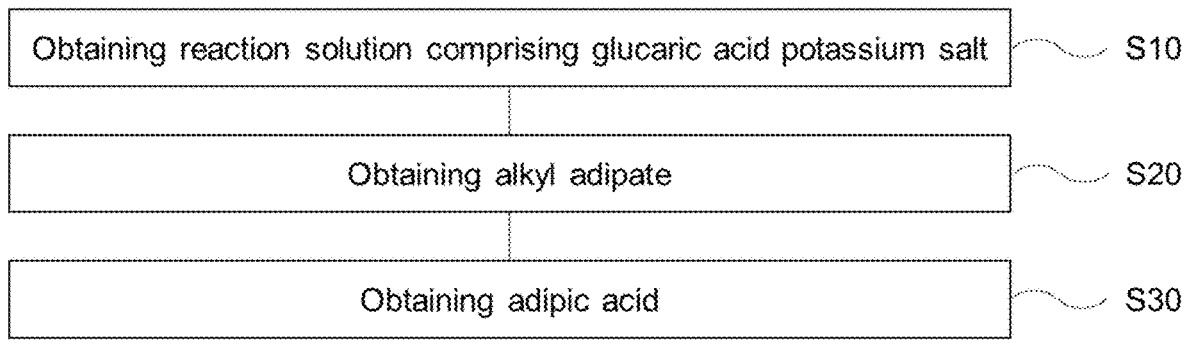
FIG. 1 is a flowchart schematically showing a process of producing adipic acid according to the present disclosure.

The above and other objects, features and advantages of the present disclosure will be more clearly understood from the following preferred embodiments taken in conjunction with the accompanying drawings. However, the present disclosure is not limited to the embodiments disclosed herein, and may be modified into different forms. These embodiments are provided to thoroughly explain the disclosure and to sufficiently transfer the spirit of the present disclosure to those skilled in the art.

Throughout the drawings, the same reference numerals will refer to the same or like elements. For the sake of clarity of the present disclosure, the dimensions of structures are depicted as being larger than the actual sizes thereof. It will be understood that, although terms such as "first", "second", etc. may be used herein to describe various elements, these elements are not to be limited by these terms. These terms are only used to distinguish one element from another element. For instance, a "first" element discussed below could be termed a "second" element without departing from the scope of the present disclosure. Similarly, the "second" element could also be termed a "first" element. As used herein, the singular forms are intended to include the plural forms as well, unless the context clearly indicates otherwise.

It will be further understood that the terms "comprise", "include", "have", etc., when used in this specification, specify the presence of stated features, integers, steps, operations, elements, components, or combinations thereof, but do not preclude the presence or addition of one or more other features, integers, steps, operations, elements, components, or combinations thereof. Also, it will be understood that when an element such as a layer, film, area, or sheet is referred to as being "on" another element, it may be directly on the other element, or intervening elements may be present therebetween. Similarly, when an element such as a layer, film, area, or sheet is referred to as being "under" another element, it may be directly under the other element, or intervening elements may be present therebetween.

Unless otherwise specified, all numbers, values, and/or representations that express the amounts of components, reaction conditions, polymer compositions, and mixtures used herein are to be taken as approximations including various uncertainties affecting measurement that inherently occur in obtaining these values, among others, and thus should be understood to be modified by the term "about" in all cases. Furthermore, when a numerical range is disclosed in this specification, the range is continuous, and includes all values from the minimum value of said range to the maximum value thereof, unless otherwise indicated. Moreover, when such a range pertains to integer values, all integers including the minimum value to the maximum value are included, unless otherwise indicated.

The current petroleum-based production process has problems such as oil price instability, use of toxic benzene, generation of environmental pollution byproducts including NOx, and the like, and thus alternative processing technology that reduces carbon emission is required and is considered as a very promising technical method. Therefore, a method of synthesizing adipic acid using a plant resource is capable of both decreasing raw material dependence on petroleum and lowering the generation of environmental pollutants.

The present disclosure intends to patent a process for first synthesizing an alkyl adipate material that may be used as an intermediate in the production of adipic acid using glucose and a process for synthesizing adipic acid thereby. This method is effective at providing an important processing route capable of synthesizing adipic acid using glucose derived from terrestrial plant resources.

FIG. 1 is a flowchart schematically showing a process of producing adipic acid according to the present disclosure. Hereinafter, the present disclosure will be described in more detail with reference to the accompanying drawings.

With reference to FIG. 1, the method of producing adipic acid according to the present disclosure may include obtaining a reaction solution by mixing a glucaric acid potassium salt, a solvent, an acid catalyst, and a catalyst for deoxydehydration at S10, obtaining alkyl adipate by adding hydrogen gas to the reaction solution and performing a deoxydehydration (DODH) reaction at S20, and obtaining adipic acid by mixing the alkyl adipate with an acid solution and performing a hydrolysis reaction at S30.

S10 is a step of obtaining a reaction solution by mixing a glucaric acid potassium salt, a solvent, an acid catalyst, and a catalyst for deoxydehydration.

A method of preparing the glucaric acid potassium salt is not limited, but may include mixing and reacting glucose, nitric acid, sodium nitrite, and potassium hydroxide, which is the general synthesis method. Accordingly, the starting material of the present disclosure may be glucose.

For example, a glucaric acid potassium salt may be prepared through a nitric acid oxidation reaction, and the molar ratio of glucose to nitric acid may be 1:2.5-3.6. Through potassium hydroxide (KOH) treatment after oxidation, a glucaric acid potassium salt may be obtained.

The solvent may include methanol or ethanol. The solvent is preferably an alcohol-like material. Other alcohol-like materials may also be applied to this reaction, but the yield may be decreased in subsequent processes.

The acid catalyst acts on the hydroxyl group of the glucaric acid potassium salt to promote a dehydration reaction.

The acid catalyst may include at least one selected from the group consisting of Amberlyst 15, 2,4-dinitrosulfonic acid, sulfuric acid, benzenesulfonic acid, trifluoromethanesulfonic acid, and p-toluenesulfonic acid, and is preferably Amberlyst-15.

The weight ratio of the glucaric acid potassium salt to the acid catalyst may be 5:7.5-8.5. If the weight ratio of the acid catalyst is less than 7.5 or is greater than 8.5, synthesis of the alkyl adipate material pursued in the present disclosure may not proceed efficiently.

The catalyst for deoxydehydration may be added after mixing the glucaric acid potassium salt and the acid catalyst, or may be added at the same time therewith.

The catalyst for deoxydehydration may be prepared, for example, by the following method. Specifically, 1.5 g of palladium(II) nitrate dihydrate and 16.18 g of potassium perrhenate are dissolved in distilled water, mixed with 60 g of activated carbon, maintained for 12 hours with stirring at 300 rpm, dried to remove distilled water, and then maintained at 400° C. for 5 hours using a catalyst calcination system.

The catalyst for deoxydehydration may include at least one selected from the group consisting of rhenium oxide and $L_xReO_y$ (in which L is amine, halogen, phenylsilyl, phosphine, alkoxy having 1 to 10 carbon atoms, alkyl having 1 to 10 carbon atoms, or COOR (in which R is an alkyl having 1 to 10 carbon atoms), and x and y are each independently an integer of 1 to 3, x+y=4).

The weight ratio of the glucaric acid potassium salt to the catalyst for deoxydehydration may be 5:3.5-4.5. If the weight ratio of the catalyst for deoxydehydration is less than 3.5 or is greater than 4.5, synthesis of the alkyl adipate material pursued in the present disclosure may not proceed efficiently.

S20 is a step of obtaining alkyl adipate by adding hydrogen gas to the reaction solution and performing a deoxydehydration (DODH) reaction.

An example of the deoxydehydration reaction in S20 may be a reaction in which four OH groups are removed and two double bonds are formed.

The hydrogen gas may be fed at a pressure of 5 bar to 20 bar.

The alkyl adipate may be represented by Chemical Formula 1, Chemical Formula 2, or Chemical Formula 3 below.

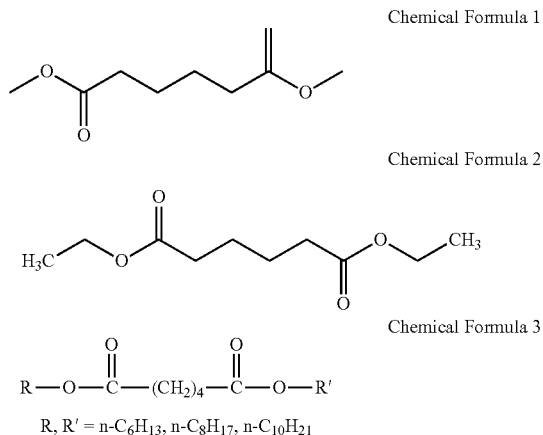

Chemical Formula 1

Chemical Formula 2

Chemical Formula 3

R, R' = n-$C_6H_{13}$, n-$C_8H_{17}$, n-$C_{10}H_{21}$ (in which n is 4, 5, 6, 7, 8, or 10.)

S20 may be performed at a temperature of 80° C. to 150° C.

S20 may be performed for a period of time of 12 hours to 24 hours. If the processing time is less than 12 hours, the reaction yield may decrease, whereas if it exceeds 24 hours, economic efficiency may be lowered.

S30 is a step of obtaining adipic acid by mixing the alkyl adipate with an acid solution and performing a hydrolysis reaction.

In S30, adipic acid may be obtained through a chemical reaction of removing only the alkyl group from alkyl adipate, and the chemical reaction may be hydrolysis. Specifically, adipic acid may be obtained through acid treatment of alkyl adipate.

An example of the reaction mechanism in S30 is a hydrolysis reaction using methyl adipate as an intermediate as represented in Scheme 1 below. For other intermediates, only the type of end group is different, but the mechanism thereof is the same.

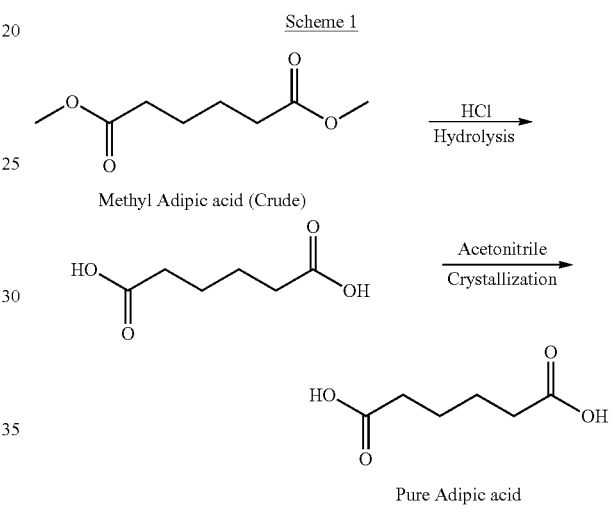

Scheme 1

Methyl Adipic acid (Crude)

Pure Adipic acid

The acid solution may include hydrochloric acid.

The concentration of the acid solution may be 1 N to 5 N. If the concentration of the acid solution exceeds 5 N, the adipic acid production yield pursued in the present disclosure may be lowered, which is undesirable.

The weight ratio of the alkyl adipate to the acid solution may be 1:5.5-6.5. If the weight ratio of the acid solution is less than 5.5 or is greater than 6.5, the adipic acid production yield pursued in the present disclosure may be lowered, which is undesirable.

S30 may be performed at a temperature of 50° C. to 100° C. If the temperature is less than 50° C. or is higher than 100° C., the adipic acid production yield pursued in the present disclosure may be lowered, which is undesirable.

A better understanding of the present disclosure may be obtained through the following examples and comparative examples. However, these examples are not to be construed as limiting the technical spirit of the present disclosure.

Examples 1 to 4 and Comparative Examples 1 to 4

Examples 1 to 4 and Comparative Examples 1 to 4 were prepared using components in the amounts shown in Table 1 below.

Preparation of Glucaric Acid Potassium Salt

The glucaric acid potassium salt used in Examples and Comparative Examples was prepared in the following manner.

10-15 g of glucose was mixed with 13 ml of 70% nitric acid ($HNO_3$). Here, the reaction temperature was 0-30° C. If the reaction temperature is less than 0° C., low reactivity may result, whereas if the reaction temperature is higher than 30° C., byproducts may be generated. Then, 10-20 mg of $NaNO_2$ was added thereto. This material induces the formation of crystals of glucaric acid, and the ratio of $NaNO_2$ to glucose is appropriately set to 1:1000. Thereafter, the reaction mixture was cooled to room temperature and basified to a pH of 9-10 as measured with pH paper using a 45% aqueous KOH solution. If the pH thereof falls out of the basic range, the salt formation effect may be deteriorated. Thereafter, the resulting mixture was acidified to a pH of 3-4 using 70% nitric acid and then allowed to precipitate at room temperature for 12 hours. The solid particles thus precipitated were filtered while washing with methanol to improve purity.

Preparation of Alkyl Adipate 5 g of the glucaric acid potassium salt was placed in a high-temperature and high-pressure chemical reaction device filled with methanol as a solvent and then mixed. Amberlyst-15, which is an acid catalyst, was slowly added thereto in the ratio shown in Table 1 below. Thereafter, a catalyst for deoxydehydration was slowly added thereto in the ratio shown in Table 1 below. Thereafter, hydrogen gas was fed thereto at 10 bar or 30 bar as shown in Table 1 below, followed by mixing with stirring at 100 rpm to 300 rpm using a stirring device. Thereafter, while maintaining the reaction temperature at 110° C., the resulting mixture was subjected to a chemical reaction for about 12 hours and then cooled to room temperature, thereby obtaining a solid material in the form of alkyl adipate such as methyl adipate or ethyl adipate.

Production of Adipic Acid

Thereafter, adipic acid was finally synthesized through hydrolysis of an alkyl group such as a methyl group or an ethyl group of the alkyl adipate using an acid solution. In this step, the concentration of the acid solution was 2 N, hydrochloric acid was used, and the weight ratio was set as shown in Table 1 below. The reaction temperature was 70° C., and the reaction time was 12 to 24 hours. Thereafter, adipic acid, which is a target product, was obtained through solid-liquid separation and purification.

Test Example 1: Confirmation of Produced Adipic Acid

In order to confirm the components of the samples prepared in Examples 1 to 4 and Comparative Examples 1 to 4, nuclear magnetic resonance (NMR) analysis was performed. NMR spectrum was analyzed using a Bruker 300 MHz analysis system.

The results thereof are shown in Table 2 below.

TABLE 2

| Classification | NMR peak position | Synthesis of adipic acid |
|---|---|---|
| Example 1 | 1.5 ppm and 2.2 ppm | ○ |
| Example 2 | 1.5 ppm and 2.2 ppm | ○ |
| Example 3 | 1.5 ppm and 2.2 ppm | ○ |
| Example 4 | 1.5 ppm and 2.2 ppm | ○ |
| Comparative Example 1 | Not observed | X |
| Comparative Example 2 | Not observed | X |
| Comparative Example 3 | Not observed | X |
| Comparative Example 4 | Not observed | X |

Figure 2:
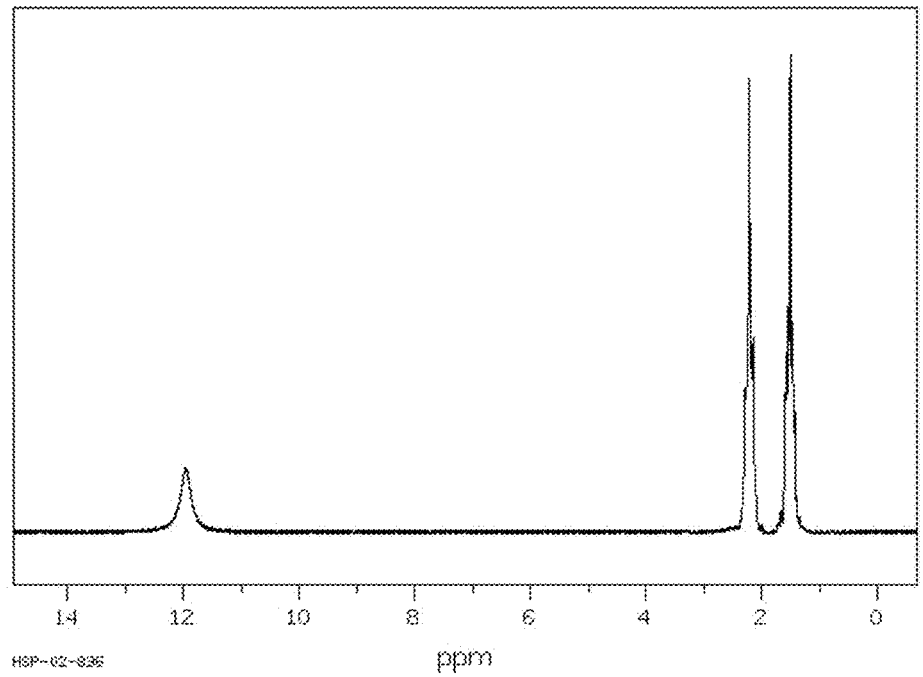
FIG. 2 is a reference view showing known results of analysis of nuclear magnetic resonance (NMR) of adipic acid.
Figure 3:
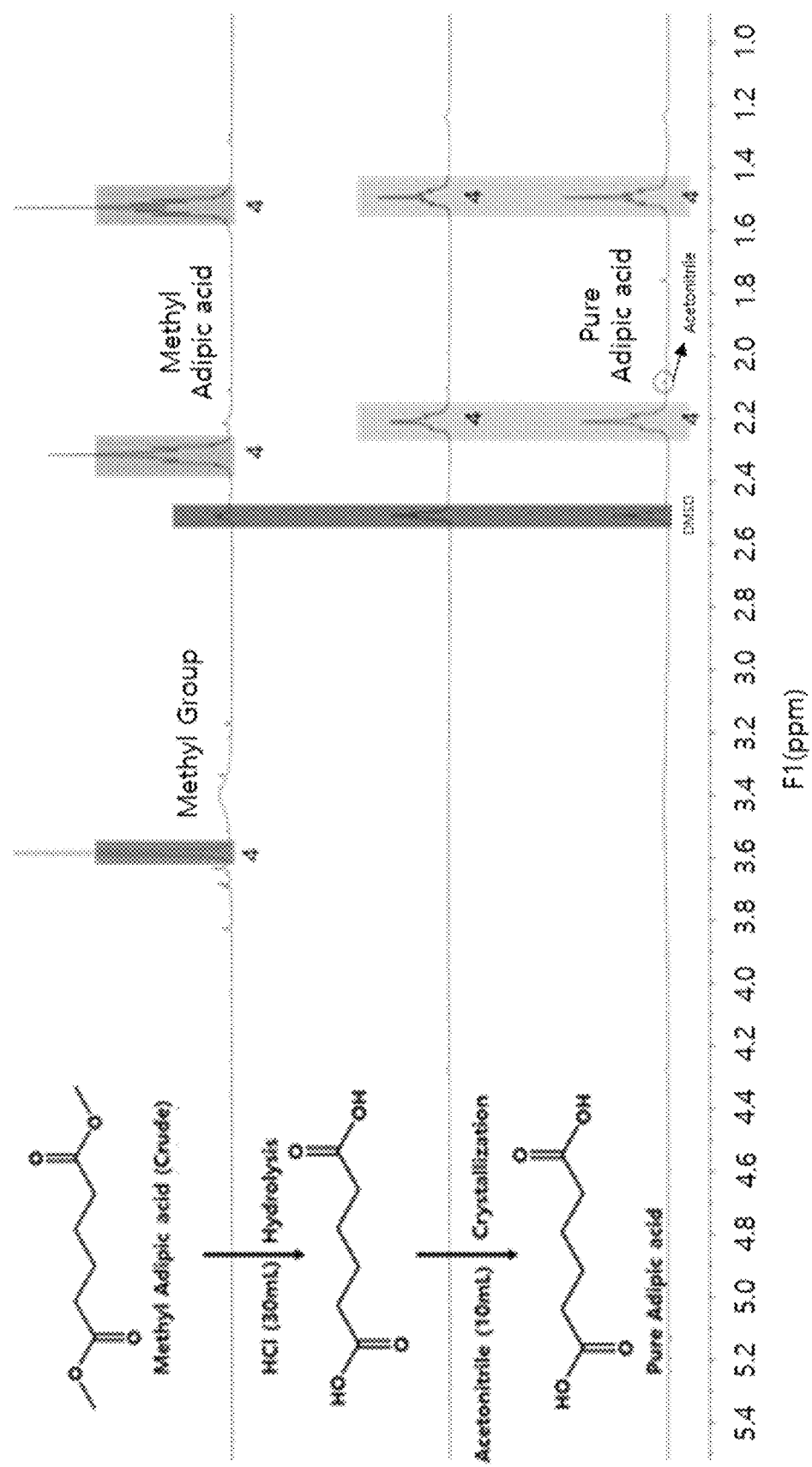
FIG. 3 shows results of analysis of $^1$H nuclear magnetic resonance ($^1$H NMR) data of adipic acid produced according to Examples of the present disclosure.
Figure 4:
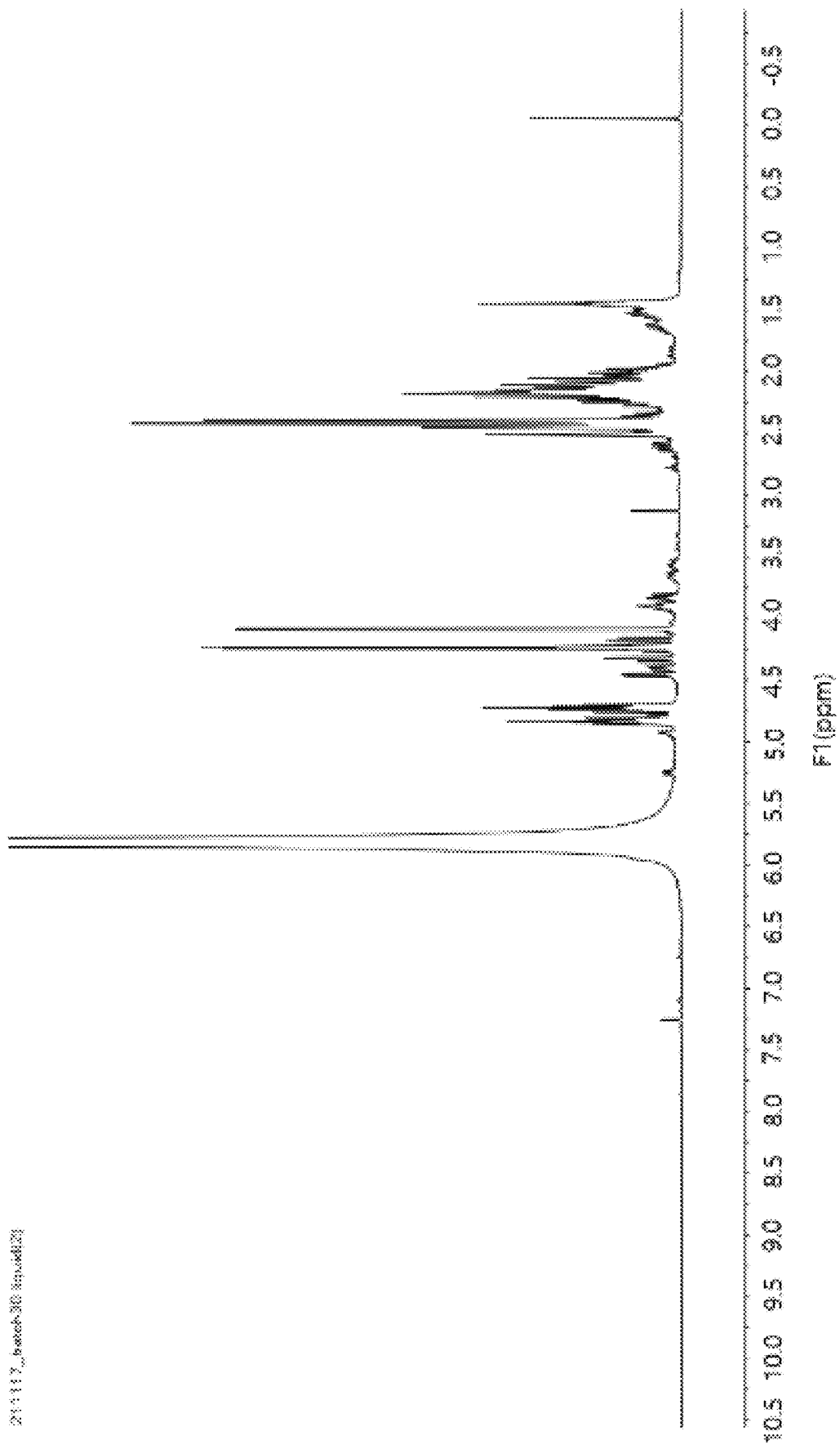
FIG. 4 shows results of analysis of $^1$H nuclear magnetic resonance ($^1$H NMR) data of adipic acid produced according to Comparative Examples of the present disclosure.

FIG. 2 is a reference view showing known results of analysis of nuclear magnetic resonance (NMR) of adipic acid. FIG. 3 shows results of analysis of $^1H$ nuclear magnetic resonance ($^1H$ NMR) data of adipic acid produced according to Examples of the present disclosure. FIG. 4 shows results of analysis of $^1H$ nuclear magnetic resonance ($^1H$ NMR) data of adipic acid produced according to Comparative Examples of the present disclosure.

As shown in FIG. 2, the most important positions were 1.5 ppm and 2.2 ppm, confirming that adipic acid was synthesized based on signals at these positions.

As shown in FIG. 3, it can be confirmed that, in Examples 1 to 4, alkyl adipate (methyl adipate) was synthesized normally according to the method of the present disclosure. Thereafter, through mixing with the acid solution and hydrolysis, the methyl groups at both ends were cleaved and disappeared, resulting in a final product, adipic acid, as confirmed by NMR analysis.

As shown in FIG. 4, it can be confirmed that, in Comparative Examples 1 to 4, a number of byproducts were generated, and the NMR peak of alkyl adipate (methyl

TABLE 1

| Classification | Example | | | | Comparative Example | | | |
|---|---|---|---|---|---|---|---|---|
|  | 1 | 2 | 3 | 4 | 1 | 2 | 3 | 4 |
| Solvent | Methanol | Methanol | Methanol | Methanol | Methanol | Methanol | Methanol | Methanol |
| Glucaric acid potassium salt:acid catalyst (weight ratio) | 5:7.5 | 5:7.6 | 5:8.0 | 5:8.5 | 5:5.5 | 5:6.5 | 5:9.5 | 5:10 |
| Glucaric acid potassium salt:catalyst for deoxydehydration (weight ratio) | 5:3.5 | 5:3.8 | 5:4.0 | 5:4.5 | 5:2.5 | 5:3.0 | 5:6.0 | 5:6.5 |
| Alkyl adipate:acid solution (weight ratio) | 1:5.5 | 1:5.8 | 1:6.0 | 1:6.5 | 1:3.5 | 1:4.0 | 1:7.0 | 1:7.5 |
| Pressure of fed hydrogen gas (S20) | 10 bar | 10 bar | 10 bar | 10 bar | 30 bar | 30 bar | 30 bar | 30 bar |
| Reaction temperature (S20) | 110° C. | 110° C. | 110° C. | 110° C. | 110° C. | 110° C. | 110° C. | 110° C. |

Glucaric acid potassium salt (Reagent sold by Sigma-Aldrich, USA)
Acid catalyst: Amberlyst-15 (Reagent sold by Sigma-Aldrich, USA)
Catalyst for deoxydehydration: prepared by the present inventors, Korea Research Institute of Chemical Technology, Hyundai Kia Motors
(Preparation method: 1.5 g of palladium(II) nitrate dihydrate and 16.18 g of potassium perrhenate are dissolved in distilled water, mixed with 60 g of activated carbon, maintained for 12 hours with stirring at 300 rpm, dried to remove distilled water, and then maintained at 400° C. for 5 hours in a catalyst calcination system.)
Acid solution: 2N hydrochloric acid (Reagent sold by Sigma-Aldrich, USA)

adipate) was not clearly observed. Even after mixing with the acid solution and hydrolysis, a number of byproducts were present, from which it can be found that normal adipic acid was not synthesized.

Therefore, the method of producing adipic acid according to the present disclosure is characterized in that glucose is used as a starting material, and adipic acid is obtained as a final material via an alkyl adipate intermediate from a glucaric acid potassium salt using glucose.

As is apparent from the above description, the present disclosure discloses a method of synthesizing adipic acid using a low-carbon material such as glucose as a plant resource, unlike a conventional method of producing adipic acid through a chemical synthesis route starting from a petrochemical material, particularly benzene.

Thereby, the production process is environmentally friendly and is also simple compared to conventional petrochemical production methods, and the amount of carbon that is emitted during the production process can be reduced.

When adipic acid produced by the present disclosure is used to prepare nylon 66 resin serving as a material for automobile parts, the carbon emission of nylon 66 resin is also reduced, ultimately contributing to carbon emission reduction of materials for automobile parts, resulting in a great industrial spillover effect.

The effects of the present disclosure are not limited to the above-mentioned effects. It should be understood that the effects of the present disclosure include all effects that can be inferred from the description of the present disclosure.

Although specific embodiments of the present disclosure have been described with reference to the accompanying drawings, those skilled in the art will appreciate that the present disclosure may be embodied in other specific forms without changing the technical spirit or essential features thereof. Thus, the embodiments described above should be understood to be non-limiting and illustrative in every way.

The invention claimed is:

1. A method of producing adipic acid, comprising:
obtaining a reaction solution by mixing a glucaric acid potassium salt, a solvent, an acid catalyst, and a catalyst for deoxydehydration;
obtaining alkyl adipate by adding hydrogen gas to the reaction solution and performing a deoxydehydration (DODH) reaction; and
obtaining adipic acid by mixing the alkyl adipate with an acid solution and performing a hydrolysis reaction.

2. The method of claim 1, wherein the glucaric acid potassium salt is obtained by mixing and reacting glucose, nitric acid, sodium nitrite, and potassium hydroxide.

3. The method of claim 1, wherein the solvent comprises at least one selected from the group consisting of methanol, ethanol and combinations thereof.

4. The method of claim 1, wherein the acid catalyst comprises at least one selected from the group consisting of Amberlyst 15, 2,4-dinitrosulfonic acid, sulfuric acid, benzenesulfonic acid, trifluoromethanesulfonic acid, and p-toluenesulfonic acid and combinations thereof.

5. The method of claim 1, wherein a weight ratio of the glucaric acid potassium salt to the acid catalyst is 5:7.5 to 8.5.

6. The method of claim 1, wherein the catalyst for deoxydehydration comprises at least one selected from the group consisting of rhenium oxide and LxReOy (in which L comprise amine, halogen, phenylsilyl, phosphine, alkoxy having 1 to 10 carbon atoms, alkyl having 1 to 10 carbon atoms, or COOR (in which R is an alkyl having 1 to 10 carbon atoms), and x and y are each independently an integer of 1 to 3, x+y=4).

7. The method of claim 1, wherein a weight ratio of the glucaric acid potassium salt to the catalyst for deoxydehydration is 5:3.5 to 4.5.

8. The method of claim 1, wherein the hydrogen gas is added at a pressure of 1 bar to 20 bar.

9. The method of claim 1, wherein the alkyl adipate is represented by Chemical Formula 1:

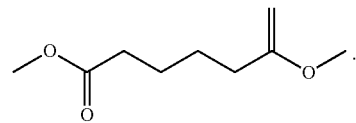

10. The method of claim 1, wherein the alkyl adipate is represented by Chemical Formula 2:

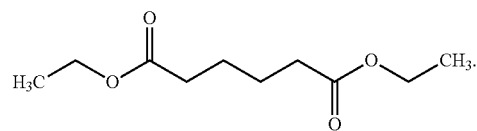

11. The method of claim 1, wherein the alkyl adipate is represented by Chemical Formula 3:

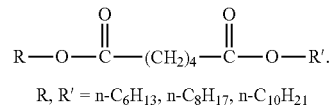

12. The method of claim 1, wherein obtaining the alkyl adipate is performed at a temperature of 80° C. to 150° C.

13. The method of claim 1, wherein obtaining the alkyl adipate is performed for a period of time of 12 hours to 24 hours.

14. The method of claim 1, wherein the acid solution comprises hydrochloric acid.

15. The method of claim 1, wherein a concentration of the acid solution is 1 N to 5 N.

16. The method of claim 1, wherein a weight ratio of the alkyl adipate to the acid solution is 1:5.5 to 6.5.

* * * * *